(12) United States Patent
Luttrull et al.

(10) Patent No.: US 9,168,174 B2
(45) Date of Patent: Oct. 27, 2015

(54) PROCESS FOR RESTORING RESPONSIVENESS TO MEDICATION IN TISSUE OF LIVING ORGANISMS

(71) Applicant: Ojai Retinal Technology, LLC, Ojai, CA (US)

(72) Inventors: Jeffrey K. Luttrull, Ojai, CA (US); Benjamin Margolis, Oakland, CA (US); David B. Chang, Tustin, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 0 days.

(21) Appl. No.: 14/607,959

(22) Filed: Jan. 28, 2015

(65) Prior Publication Data

US 2015/0157498 A1    Jun. 11, 2015

Related U.S. Application Data

(63) Continuation-in-part of application No. 13/798,523, filed on Mar. 13, 2013, which is a continuation-in-part of application No. 13/481,124, filed on May 25, 2012.

(51) Int. Cl.
*A61N 5/06* (2006.01)
*A61F 9/008* (2006.01)
(Continued)

(52) U.S. Cl.
CPC ............ *A61F 9/00821* (2013.01); *A61B 18/20* (2013.01); *A61F 9/008* (2013.01); *A61F 9/00817* (2013.01); *A61F 2009/00863* (2013.01); *A61N 5/06* (2013.01); *A61N 5/1017* (2013.01); *A61N 2005/0648* (2013.01)

(58) Field of Classification Search
CPC . A61F 9/00821; A61F 9/008; A61F 9/00817; A61F 2009/00863; A61N 5/06; A61N 5/1017; A61B 18/20
USPC ........................................ 606/2, 4; 607/88, 89
See application file for complete search history.

(56) References Cited

U.S. PATENT DOCUMENTS

| 3,408,593 | A | 10/1968 | Hurwitz, Jr. |
| 4,048,011 | A | 9/1977 | Kovin et al. |
| 4,176,325 | A | 11/1979 | Kajimura et al. |

(Continued)

FOREIGN PATENT DOCUMENTS

| WO | 2006005038 | A2 | 1/2006 |
| WO | 2007035855 | A2 | 3/2007 |
| WO | 2007106521 | A2 | 9/2007 |

OTHER PUBLICATIONS

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

(Continued)

*Primary Examiner* — Aaron Roane
(74) *Attorney, Agent, or Firm* — Kelly & Kelley, LLP

(57) ABSTRACT

A process for restoring responsiveness to medication in eye tissue, namely retinal tissue, that is unresponsive to medication. The process utilizes a laser source for generating a confluent, contiguous laser light beam. The laser light beam is preferably a subthreshold diode micropulse laser beam which is optically shaped through an optical lens or mask. The tissue is then exposed to the confluent, contiguous laser light beam and allowed to recover for thirty days before administering medication to which the tissue was unresponsive.

18 Claims, 7 Drawing Sheets

(51) Int. Cl.
*A61N 5/10* (2006.01)
*A61B 18/20* (2006.01)

(56) References Cited

U.S. PATENT DOCUMENTS

| | | | |
|---|---|---|---|
| 4,194,114 A | 3/1980 | Pankratov et al. | |
| 4,410,365 A | 10/1983 | Glukhovsky et al. | |
| 4,695,733 A | 9/1987 | Pesavento | |
| 4,730,335 A | 3/1988 | Clark et al. | |
| 4,791,634 A | 12/1988 | Miyake | |
| 4,865,029 A | 9/1989 | Pankratov et al. | |
| 4,879,722 A | 11/1989 | Dixon et al. | |
| 4,930,504 A | 6/1990 | Diamantopoulos et al. | |
| 4,933,944 A | 6/1990 | McGraw | |
| 4,935,931 A | 6/1990 | McGraw | |
| 4,961,079 A | 10/1990 | Owens et al. | |
| 4,967,416 A | 10/1990 | Esterowitz et al. | |
| 5,037,421 A | 8/1991 | Boutacoff et al. | |
| 5,067,951 A | 11/1991 | Greve | |
| 5,085,492 A | 2/1992 | Kelsoe et al. | |
| 5,088,803 A | 2/1992 | Buzawa | |
| 5,147,354 A | 9/1992 | Boutacoff et al. | |
| 5,372,595 A | 12/1994 | Gaasterland et al. | |
| 5,394,199 A | 2/1995 | Flower | |
| 5,430,756 A | 7/1995 | Hanihara | |
| 5,520,680 A | 5/1996 | Shapshay et al. | |
| 5,651,019 A | 7/1997 | Goldberg et al. | |
| 5,982,789 A | 11/1999 | Marshall et al. | |
| 6,050,990 A * | 4/2000 | Tankovich | A61B 18/203 606/16 |
| 6,066,128 A | 5/2000 | Bahmanyar et al. | |
| 6,208,769 B1 | 3/2001 | Pankratov | |
| 6,222,869 B1 | 4/2001 | Marshall et al. | |
| 6,327,291 B1 | 12/2001 | Marshall | |
| 6,377,599 B1 | 4/2002 | Marshall | |
| 6,540,391 B2 | 4/2003 | Lanzetta et al. | |
| 6,681,185 B1 | 1/2004 | Young et al. | |
| 6,715,877 B2 | 4/2004 | Molebny | |
| 6,733,490 B1 | 5/2004 | Falsini et al. | |
| 6,813,942 B1 | 11/2004 | Vozhdaev et al. | |
| 6,889,695 B2 | 5/2005 | Pankratov et al. | |
| 7,227,196 B2 | 6/2007 | Burgener, II et al. | |
| 7,387,785 B1 | 6/2008 | Rudin et al. | |
| 7,452,081 B2 | 11/2008 | Wiltberger et al. | |
| 7,645,276 B2 | 1/2010 | Pankratov et al. | |
| 7,763,828 B2 | 7/2010 | Talwar et al. | |
| 7,766,903 B2 * | 8/2010 | Blumenkranz | A61F 9/008 606/10 |
| 7,766,904 B2 | 8/2010 | Mc Gowan, Sr. et al. | |
| 7,771,417 B2 | 8/2010 | Telfair et al. | |
| 7,909,816 B2 | 3/2011 | Buzawa | |
| 2002/0120255 A1 | 8/2002 | Sotiropoulos et al. | |
| 2008/0015553 A1 | 1/2008 | Zacharias | |
| 2010/0152716 A1 | 6/2010 | Previn et al. | |
| 2010/0168724 A1 | 7/2010 | Sramek et al. | |
| 2010/0249760 A1 | 9/2010 | Blumenkranz et al. | |
| 2010/0290007 A1 | 11/2010 | Van de Velde | |
| 2011/0196350 A1 | 8/2011 | Friedman et al. | |

OTHER PUBLICATIONS

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

* cited by examiner

PROCESS FOR RESTORING RESPONSIVENESS TO MEDICATION IN TISSUE OF LIVING ORGANISMS

RELATED APPLICATION

This application is a continuation-in-part of U.S. application Ser. No. 13/798,523, filed Mar. 13, 2013.

FIELD OF THE INVENTION

The present invention generally relates to phototherapy or photostimulation of biological tissue. More particularly, the present invention is directed to a method of laser adjuvant therapy treatment for protection and disease prevention in living tissue, including a method of sub-threshold diode micropulse (SDM) laser therapy for the sensitization or re-sensitization of medically unresponsive or diseased tissue, particularly retinal and similar tissue.

BACKGROUND OF THE INVENTION

Medical use of lasers is a long-standing and well known practice. Uses include photocoagulation (burning or scarification); photodisruption (explosive destruction of tissue); photolysis (cutting or separation of tissue); phototherapy (generation of photochemical effects including ionization and breakage of molecular bonds); photostimulation (inducing molecular aggregation, conformation change, pH change, usually via induced tissue hyperthermia); and photodynamic therapy (laser-induced activation or catalysis of a photosensitive pharmacologic agent). Photocoagulation, photodisruption, photolysis, phototherapy, and photostimulation all describe direct effects of a laser on tissue to achieve a therapeutic effect. These laser-induced therapeutic effects may be employed separately, or in combination with any other therapeutic measure including but not limited to surgery, drug therapy, gene therapy, stem-cell therapy, etc. In photodynamic therapy the laser produces little to no effect of its own and by itself is therapeutically ineffective. Instead, the therapeutic effect of the laser in photodynamic therapy is simply to activate a photo-sensitive drug which is also, by itself, therapeutically ineffective and/or inactive. Thus, the target of the laser in photodynamic therapy is not the tissue or organism, but the drug which has been introduced into the tissue or organism.

With reference now to FIG. 1, a diagrammatic view of an eye, generally referred to by the reference number 10, is shown. When using phototherapy, the laser light is passed through the patient's cornea 12, pupil 14, and lens 16 and directed onto the retina 18. The retina 18 is a thin tissue layer which captures light and transforms it into the electrical signals for the brain. It has many blood vessels, such as those referred to by reference number 20, to nourish it. Various retinal diseases and disorders, and particularly vascular retinal diseases such as diabetic retinopathy, are treated using conventional thermal retinal photocoagulation, as discussed above. The fovea/macula region, referred to by the reference number 22 in FIG. 1, is a portion of the eye used for color vision and fine detail vision. The fovea is at the center of the macula, where the concentration of the cells needed for central vision is the highest. Although it is this area where diseases such as age-related macular degeneration are so damaging, this is the area where conventional photocoagulation phototherapy cannot be used as damaging the cells in the foveal area can significantly damage the patient's vision. Thus, with conventional photocoagulation therapies, the foveal region is avoided.

Photobiology teaches that near-infrared (NIR) lasers have little effect on healthy cells, but tend to restore, by various means, normal function to diseased cells or cells made dysfunctional by pathologic or abnormal environments such as disease. NIR can do this without damaging the cell in any way, instead revitalizing the cell. The inventors proposed this as the mechanism of action of high-density, low-intensity subthreshold diode micropulse laser (SDM), shown to be an effective therapy for retinal diseases, including diabetic retinopathy (see U.S. Publication No. 2013/0317570). In this sense SDM is a clinically harmless form of retinal photo-stimulation or phototherapy.

Turning to medication therapy, no drug is always effective, and despite initial efficacy, drug tolerance may develop. Due to biologic complexity, safe and effective targeted drug therapy like vascular endothelial growth factor inhibitors (anti-VEGF) medication is difficult and expensive to develop, generally narrow in focus, and often offered late in the disease process due to treatment risks, adverse effects, and expense. Despite application to chronic conditions, drugs are typically short acting. Exemplified by current intravitreal anti-VEGF agents for retinal disease, drug therapy may present extraordinary burdens in terms of clinical access, social resources and economic costs. Thus, despite the great benefits of modern pharmacotherapy, its future as a sustainable global disease management strategy for common and important diseases, including age-related macular degeneration (ARMD) and diabetic retinopathy, appears inevitably limited. Such considerations underscore the need for more widely applicable and accessible treatments. Early and preventive treatments will offer the greatest benefits.

Drug therapy of various disease states is often associated with tachyphylaxis or drug tolerance. In these instances, the target tissue of the drug becomes less or completely unresponsive to the drug effects despite initial effectiveness. Various mechanisms for these processes have been proposed. Drug tolerance is the most common cause of treatment failure in eyes with neurovascular, age-related, macular degeneration (NAMD). The development of drug tolerance may cause failure of treatment medication. Drug tolerance is most often addressed by changing drug dosage (generally increasing); changing drugs; or adding new drugs directed at suppressing the cause of drug unresponsiveness. For instance, in some cases, drug tolerance is thought to be due to an immunologic response to the drug. Thus, additional drugs may be tried to suppress the immune response, permitting the primary drug therapy to become effective once again. However, in many cases none of these options to address unresponsiveness are either available or effective. In such situations treatment is rendered ineffective with subsequent loss of function or life.

A common example of drug tolerance is the treatment of age-related choroidal neovascularization complicating macular degeneration ("wet" ARMD) with various anti-VEGF medications. Pharmacologic inhibitors of VEGF have become the mainstay of treatment for NAMD. They are currently the most effective intervention to reduce macular exudation, choroidal neovascular membrane (CNVM) growth, and most importantly, the risk of visual loss. Thus, ineffectiveness of anti-VEGF medication presents a serious and sight-threatening problem for which there are currently no comparably effective alternatives. Current intravitreal anti-VEGF medications employ pharmacologic (large) doses of medication designed to temporarily remove, by binding, VEGF from the vitreous cavity, retina and submacular space.

The main source of VEGF in the retina is the retinal pigment epithelium (RPE). VEGF production is linked to expression of many other factors, the absolute levels and balance of which may be altered with great effect in various disease states, and in response to various treatments, including drugs and retinal laser treatment.

Anti-VEGF injections, typically administered on a near-monthly basis for years, tend to lose effectiveness with repeated use. Use of higher dosages may temporarily improve effectiveness in some cases. The gradual loss of drug effect that may, at times, respond to increased drug dosing—drug tolerance—is generally a permanent condition. This is distinguished from "tachyphylaxis", in which the loss of drug response tends to develop almost immediately, is not dose-dependent, and may resolve after a period of non-treatment. Thus, "tolerance" appears to best describe the typical loss of response to anti-VEGF treatment of NAMD; and the development of proliferative disease in some eyes despite long-term therapy for diabetic macular edema (DME). Some patients who become unresponsive (tolerant) to one anti-VEGF drug will respond to a different anti-VEGF drug. However, some of these patients eventually become tolerant and unresponsive to all available anti-VEGF medications. Photodynamic therapy with medications such as Verteporfin has been reported to be beneficial as "rescue therapy" in such cases. But, at this point in time, loss of anti-VEGF monotherapy effectiveness generally bodes ill for the visual prognosis.

In the example of "wet" ARMD treatment, one mechanism for the development of tolerance/tachyphylaxis to drugs is "up-regulation". Typically, drug treatment employs dosages of chemicals that are biologically active but administered in massive quantities compared to the physiologic production of biochemicals normally produced in the body tissues. A common example is VEGF, which is a cytokine (powerful locally acting extracellular protein) produced by various ocular tissues including the neurosensory retina and retinal pigment epithelium. As a normal and innate cytokine, VEGF is associated with both salutary and pathologic effects, depending on the tissue and setting. In "wet" ARMD, VEGF production is pathologically locally elevated by, or causing, the disease process and massive intraocular dosages of anti-VEGF medications are used to bind and/or block VEGF or its action, resulting in a positive therapeutic effect. It has been shown that serial administration of anti-VEGF agents in "wet" ARMD results in progressively less robust therapeutic effectiveness. In some patients, anti-VEGF drugs stop working all together and, absent other effective therapy, loss of vision ensues.

It has been proposed that by repeatedly and chronically extinguishing VEGF produced by retinal tissue, anti-VEGF medications induce the target tissue, by feedback mechanisms, to increase VEGF production. While this "up-regulated" VEGF production may continue to be effectively neutralized by massive and repeated doses of anti-VEGF drug, other clinically harmful effects may occur that are not addressed by the typically narrowly focused inciting drug. For instance, VEGF production is often tied to production of other cytokines which may have similarly potentially clinically harmful effects, such as interleukins (IL) or tissue matrix metalloproteinases (TMMP); and is often associated with decreased production of potentially beneficial cytokines such as Pigment Epithelial Derived Factor (PEDF). It is thought that drug-induced alteration in the cellular expression of these and possibly many other cytokines and other factors known and unknown may be one cause of tolerance/tachyphylaxis observed in the treatment of "wet" ARMD with anti-VEGF drugs. Thus, in this case, initially effective drug therapy has induced a specific state of retinal abnormality eventually rendering the drug ineffective.

Elaboration of cytokines (such as VEGF, IL, TMMP, PEDF, etc) by the retinal pigment epithelium is thought to be a prime driver and determinant of retinal disease. Thus it is reasonable to hypothesize that "normalization of retina function" might include a return toward the cytokine production profiles characteristic of native, normal retina. Thus, in diabetes mellitus, exposure to chronic hyperglycemia and attendant endocrine disturbances may induce chemical changes within the retinal pigment epithelium that lead to altered cytokine expression and a subsequent dysfunction and/or dysregulation of the retina defined as a disease state (diabetic retinopathy).

General laser treatment of the retina for various disorders has been employed for over 50 years. Traditionally, laser photocoagulation characterized by intentional laser-induced thermal destruction and scarification of the retina, has been employed. Due to the clinical effectiveness of retinal laser photocoagulation, the long-held view in medicine was that the beneficial effects of treatment were due to the retinal damage created by photocoagulation. In 2000, one of the named inventors developed a new method of retinal laser treatment (SDM) that did not employ photocoagulative tissue damage or destruction. He demonstrated therapeutically effective treatment of diabetic macular edema (DME) without laser-induced retinal damage or adverse treatment effect detectable by any means presently known. His findings revealed that prior theories of laser mechanism of action for retinal vascular disease, such as diabetic retinopathy, were incorrect as they assumed laser-induced retinal damage as a prerequisite for therapeutic effectiveness. Subsequently, he proposed a new mechanism of retinal laser action based on his observations of SDM. He proposed that SDM worked by "normalizing" retinal function without cellular damage or injury, much as has been shown in prior work in other tissues examined in photobiology. This might occur in many ways including those as yet unknown.

Accordingly, there is a need for a treatment method for the sensitization or re-sensitization of medically unresponsive or diseased tissue. The present invention fulfills these needs and provides other related advantages.

SUMMARY OF THE INVENTION

The present invention is directed to a process for restoring responsiveness to medication in tissue of living organisms that is unresponsive to medication. A laser source is used to generate a confluent, contiguous laser light beam. The laser light beam is optically shaped through an optical lens or mask. The tissue is then exposed to the confluent, contiguous laser light beam and allowed to recover for a predetermined period of time before administering medication to which the tissue was unresponsive. The predetermined period of time is preferably one month.

The tissue preferably comprises retinal tissue, fovea and foveola, retinal pigment epithelium, choroidal neovascular membrane, subretinal fluid, macula, parafovea, and/or perifovea. In this instance, the process includes the step of dilating a pupil of an eye containing the tissue. The process further includes applying topical proparacaine to a cornea of the eye. The process may also include applying a macular contact lens with viscoelastic fluid, wherein the macular contact lens has a magnification factor of 1.05×. The exposing step includes exposing the laser light beam to the entire retina and fovea.

The confluent, contiguous laser light beam preferably comprises a subthreshold diode micropulse laser beam. The subthreshold diode micropulse laser beam preferably has a high-density comprising between 400 and 1200 spots in a 300 micron treatment area. The subthreshold diode micropulse laser beam also preferably has a wavelength between 750 nm-1300 nm at 2.0 Watts. More particularly, the wavelength is approximately 810 nm.

The subthreshold diode micropulse laser beam preferably has a duty cycle of less than 10% and a 0.02 second exposure duration. More preferably, the duty cycle is approximately 5%. The subthreshold diode micropulse laser beam has a pulse length of 500 milliseconds or less. More preferably the pulse length is 20 milliseconds.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention is directed to a novel medical laser application termed "laser sensitization", "laser re-sensitization", or "laser adjuvant therapy" (LAT) using SDM laser treatments. Uniquely in LAT, the target of the laser application is tissue rather than the drug that is activated by the laser. However, it is not expected in LAT that application of the laser will necessarily have any significant or even notable therapeutic effect alone. Instead, laser treatment of the target tissue is designed and intended to make the tissue responsive or restore responsiveness to other therapeutically effective treatments such as but not limited to drug therapy.

Conventional thinking assumes that the physician must intentionally create retinal damage as a prerequisite to therapeutically effective treatment. With reference to FIG. 2, FIGS. 2A-2F are graphic representations of the effective surface area of various modes of retinal laser treatment for retinal vascular disease. The gray background represents the retina 30 which is unaffected by the laser treatment. The black areas 32 are areas of the retina which are destroyed by conventional laser techniques. The lighter gray or white areas 34 represent the areas of the retina affected by the laser, but not destroyed.

Figure 1:
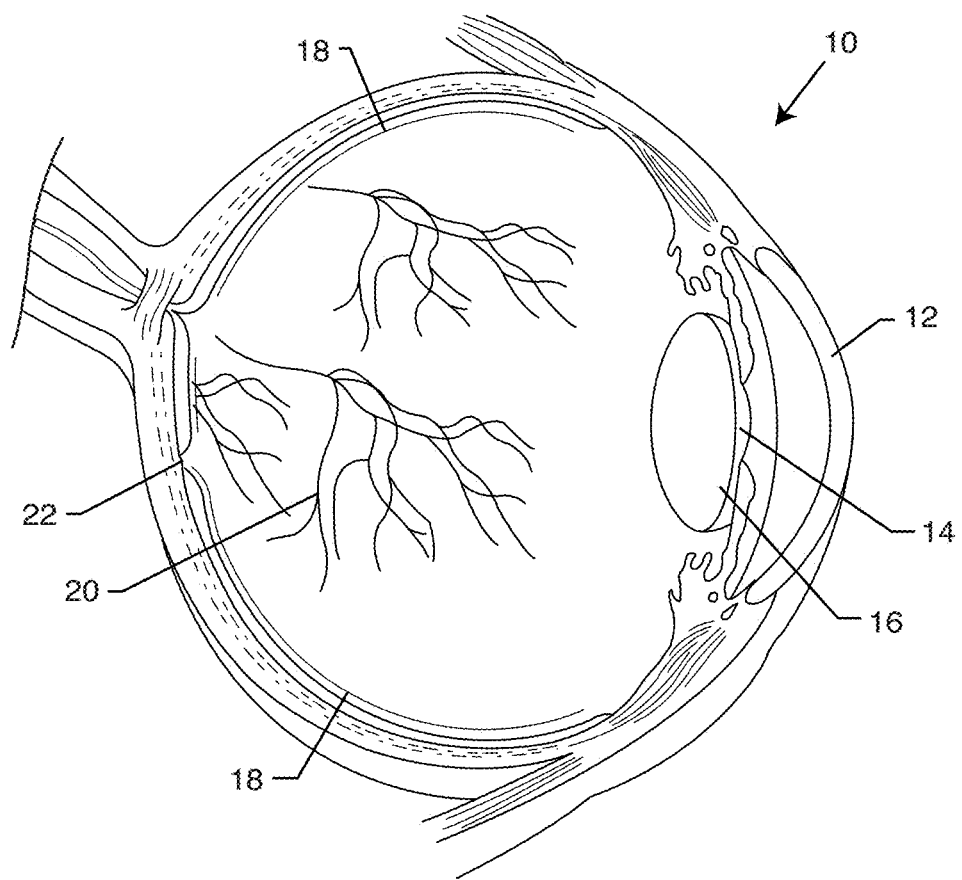
FIG. 1 is a cross-sectional diagrammatic view of a human eye.
Figure 2A:
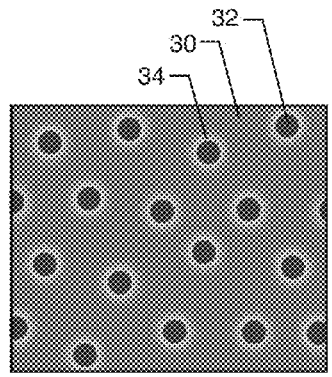
FIGS. 2A-2F are graphic representations of the effective surface area of various modes of retinal laser treatment.

FIG. 2A illustrates the therapeutic effect of conventional argon laser retinal photocoagulation. The therapeutic effects attributed to laser-induced thermal retinal destruction include reduced metabolic demand, debulking of diseased retina, increased intraocular oxygen tension and ultra-production of vasoactive cytokines, including vascular endothelial growth factor (VEGF).

Figure 2B:
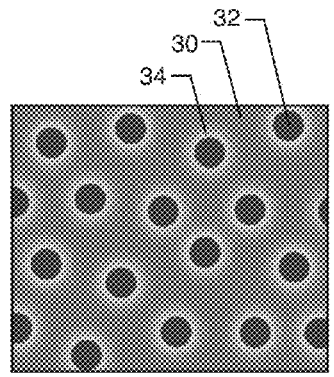
Figure 2C:
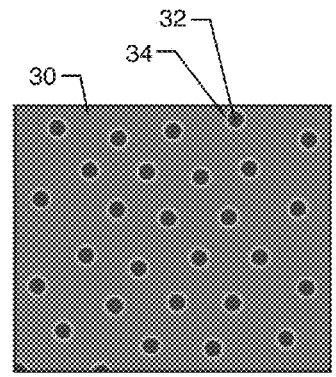

With reference to FIG. 2B, increasing the burn intensity of the traditional laser burn is shown. It will be seen that the burned and damaged tissue area 32 is larger, which has resulted in a larger "halo effect" of heated, but undamaged, surrounding tissue 34. Laboratory studies have shown that increased burn intensity is associated with an enhanced therapeutic effect, but hampered by increased loss of functional retina and inflammation. However, with reference to FIG. 2C, when the intensity of the conventional argon laser photocoagulation is reduced, the area of the retina 34 affected by the laser but not destroyed is also reduced, which may explain the inferior clinical results from lower-intensity/lower-density or "mild" argon laser grid photocoagulation compared to higher-intensity/higher-density treatment, as illustrated in FIG. 2B.

Figure 2D:
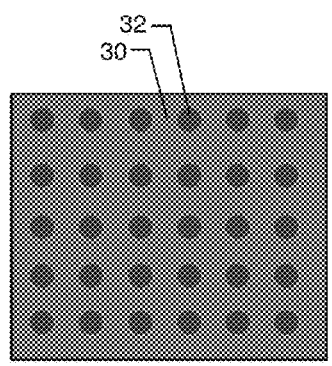

With reference to FIG. 2D, it has been found that low-fluence photocoagulation with short-pulse continuous wave laser photocoagulation, also known as selective retinal therapy, produces minimal optical and lateral spread of laser photothermal tissue effects, to the extent that the area of the retina affected by the laser but not destroyed is minimal to nonexistent. Thus, despite damage or complete ablation of the directly treated retina 30, the rim of the therapeutically affected and surviving tissue is scant or absent. This explains the recent reports finding superiority of conventional argon laser photocoagulation over PASCAL for diabetic retinopathy.

However, the inventors have shown that such thermal retinal damage is unnecessary and questioned whether it accounts for the benefits of the conventional laser treatments. Instead, the therapeutic alterations in the retinal pigment epithelium (RPE) cytokine production elicited by conventional photocoagulation comes from cells at the margins of traditional laser burns, affected but not killed by the laser exposure, referred to by the reference number 34 in FIG. 2.

Figure 2E:
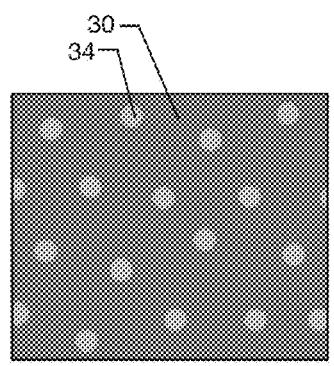

FIG. 2E represents the use of a low-intensity and low-density laser, such as a micropulsed diode laser. This creates subthreshold retinal photocoagulation, shown by the reference number 34, without any visible burn areas 32. All areas of the retinal pigment epithelium exposed to the laser irradiation are preserved, and available to contribute therapeutically.

The present invention relates to a system and process for restoring responsiveness to medication in medication-tolerant tissue, by means of high-density/low-intensity subthreshold diode micropulse laser treatment. The inventors have undertaken to study the use of high-density and low-intensity, subthreshold diode micropulsed lasers in the treatment of bodily tissues such as retinas or other similar tissues. In this context, such treatment creates subthreshold stimulation without any visible burn areas. All areas of the tissue exposed to the subthreshold laser irradiation are preserved, and available to contribute therapeutically.

High-density/low-intensity subthreshold diode micropulse laser treatment (SDM), which by definition does not produce laser-induced retinal damage and has no known adverse treatment effect, has been reported to be an effective treatment in a number of retinal disorders. These include diabetic macular edema (DME), proliferative diabetic retinopathy (PDR), macular edema due to branch retinal vein occlusion (BRVO), and central serous chorioretinopathy (CSR). The safety of SDM is such that it may be used transfoveally in eyes with 20/20 visual acuity to reduce the risk of visual loss due to early fovea-involving DME. The system would also include a fail-safe design such that failure renders it ineffective, not dangerous. Operating at maximum output, the inventive system would remain harmless, i.e., without any adverse treatment effect, and therapeutically effective.

One of the hottest areas presently in retinal research is the treatment of geographic atrophy, which is the most sight-threatening and aggressive form of dry age-related macular degeneration (AMD). The inventors have found that SDM treatment of patients suffering from AMD can slow the progress or even stop the progression of AMD. Most of the patients have seen subjective improvement after the SDM treatment with some experiencing better vision. It is believed that SDM works by targeting, preserving, and "normalizing" (moving toward normal) function of the retinal pigment epithelium (RPE).

SDM was able to stop or reverse the manifestations of the diabetic retinopathy disease state without treatment-associated damage or adverse effects, despite the persistence of systemic diabetes mellitus. On this basis it is hypothesized that SDM might work by inducing a return to more normal cell function and cytokine expression in diabetes-affected RPE cells, analogous to hitting the "reset" button of an electronic device to restore the factory default settings.

The inventors believe that use of the laser, or any radiant or other energy, on any tissue, organ or part or area of the body, primarily or even solely to promote or restore and thus potentially maintain the effectiveness of drug or other therapy constitutes a novel medical treatment not previously described. As an "adjuvant" may be defined as a treatment whose only benefit or effect is to actuate or potentiate another therapeutically effective treatment, "Laser Adjuvant Therapy" or LAT, may be used to describe this novel treatment.

The American Standards Institute (ANSI) has developed standards for safe workplace laser exposure based on the combination of theoretical and empirical data. The "maximum permissible exposure" (MPE) is the safety level, set at approximately $1/10^{th}$ of the laser exposure level expected to produce biological effects. At a laser exposure level of 1 times MPE, absolute safety would be expected and retinal exposure to laser radiation at this level would be expected to have no biologic affect. Based on ANSI data, a 50% of some risk of suffering a barely visible (threshold) burn is generally encountered at 10 times MPE for conventional continuous wave laser exposure. For a low-duty cycle micropulsed laser exposure of the same power, the risk of threshold burn is approximately 100 times MPE. Thus, the therapeutic range— the interval of doing nothing at all and the 50% of some likelihood of producing a threshold burn—for low-duty cycle micropulsed laser irradiation is 10 times wider than for continuous wave laser irradiation with the same energy. It has been determined that safe and effective subthreshold photocoagulation using a micropulsed diode laser is between 18 times and 55 times MPE, with a preferred laser exposure, for example, to retinal tissue at 47 times MPE for a near-infrared 810 nm diode laser. At this level, it has been observed that there is therapeutic effectiveness with no discernible retinal damage whatsoever.

It has been found that the intensity or power of a laser between 100 watts to 590 watts per square centimeter is effective yet safe. A particularly preferred intensity or power of the laser light is approximately 350 watts per square centimeter for an 810 nm micropulsed diode laser.

Power limitations in current micropulsed diode lasers require fairly long exposure duration. The longer the exposure, the more important the center-spot heat dissipating ability toward the unexposed tissue at the margins of the laser spot and toward the underlying choriocapillaris as in the retina. Thus, the micropulsed laser light beam of an 810 nm diode laser should have an exposure envelope duration of 500 milliseconds or less, and preferably approximately 300 milliseconds. Of course, if micropulsed diode lasers become more powerful, the exposure duration should be lessened accordingly.

Another parameter of the present invention is the duty cycle (the frequency of the train of micropulses, or the length of the thermal relaxation time in between consecutive pulses). It has been found that the use of a 10% duty cycle or higher adjusted to deliver micropulsed laser at similar irradiance at similar MPE levels significantly increase the risk of lethal cell injury, particularly in darker fundi. However, duty cycles less than 10%, and preferably approximately 5% duty cycle (or less) demonstrated adequate thermal rise and treatment at the level of the MPE cell to stimulate a biologic response, but remained below the level expected to produce lethal cell injury, even in darkly pigmented fundi. Moreover, if the duty cycle is less than 5%, the exposure envelope duration in some instances can exceed 500 milliseconds.

In a particularly preferred embodiment, small laser spots are used. This is due to the fact that larger spots can contribute to uneven heat distribution and insufficient heat dissipation within the large laser spot, potentially causing tissue damage or even tissue destruction towards the center of the larger laser spot. In this usage, "small" would generally apply to spots less than 1 mm in diameter. However, the smaller the spot, the more ideal the heat dissipation and uniform energy application becomes. Thus, at the power intensity and exposure duration described above, small spots, such as along the size of the wavelength of the laser, or small geometric lines or other objects are preferred so as to maximize even heat distribution and heat dissipation to avoid tissue damage.

Thus, the following key parameters have been found in order to create harmless, "true" subthreshold photocoagulation in accordance with the present invention: a) a low (preferably 5% or less) duty cycle; b) a small spot size to minimize heat accumulation and assure uniform heat distribution within a given laser spot so as to maximize heat dissipation; c) sufficient power to produce laser exposures of between 18 times-55 times MPE producing a temperature rise of no more than 7° C.-14° C.; and irradiance of between 100-590 W/cm².

Figure 2F:
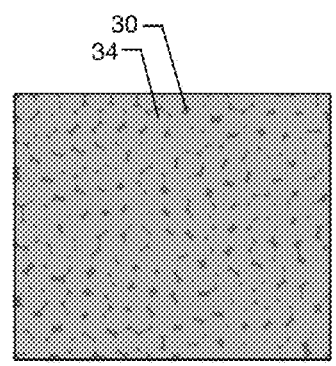

Using the foregoing parameters, a harmless, "true" subthreshold photocoagulation phototherapy treatment can be attained which has been found to produce the benefits of conventional photocoagulation phototherapy, but avoids the drawbacks and complications of conventional phototherapy. In fact, "true" subthreshold photocoagulation phototherapy in accordance with the present invention enables the physician to apply a "low-intensity/high-density" phototherapy treatment, for example as illustrated in FIG. 2F for treatment of the entire retina, including sensitive areas such as the macula and even the fovea without creating visual loss or other damage. As indicated above, using conventional phototherapies was impossible on the entire retina, particularly the fovea, as it would create vision loss due to the tissue damage in sensitive areas.

An analysis of the effectiveness and safety of the discussed SDM treatment has been performed with approximations to the exact equations for the laser absorption, heat diffusion, and Arrhenius reaction rates describing the process. Comparisons have also been made with the same approximate equations for alternate approaches (CW and Pascal and nanosecond CW laser exposures). The following indicates that for typical operating parameters, SDM is both safe and effective, whereas the alternate techniques can be either ineffective or not safe.

Results for Arrhenius Integrals from Approximate Equations

TABLE 1

Four typical laser treatments

| Laser parameters type | Retinal spot diameter (μm) | Laser power (mW) | Exposure time (ms) | Duty Cycle (repeat rate) |
|---|---|---|---|---|
| Canonical SDM | 131 | 950 | 300 | 5% (500 Hz) |
| CW power equiv to SDM | 131 | 47.5 | 300 | 100% |
| CW temps equiv to SDM | 131 | 37 | 300 | 100% |
| CSMO Pascal | 100 | 133 | 20 | 100% |

In the first four cases, the laser wavelength is 810 nm, while in the Pascal case, the wavelength is 532 nm. The absorption coefficient for 532 nm is approximately 4 times that for 810 nm.

The Arrhenius integral results for damage and HSP production for these four treatments are summarized in Table 2.

TABLE 2

Arrhenius integral results for the treatments of Table 1 (using our approximate equations).

| Laser parameters type | dTp | dToo | Ω (dmg) | Ω (HSP) |
|---|---|---|---|---|
| Canonical SDM | 10.97 | 9.38 | 0.37 | $2.2 \times 10^7$ |
| CW power equiv to SDM | 12.03 | | 0.0035 | 0.09 |
| CW temps equiv to SDM | 9.38 | | 0.0018 | 0.0004 |
| CSMO Pascal | 176 | | $1.86 \times 10^9$ | $2.33 \times 10^{94}$ | dTp is the temperature rise of the first pulse (and only pulse, for the 3 CW parameters).
dToo is the baseline temperature rise of the pulse train for SDM.
Ω (dmg) is the arrhenius integral for damage using the Arrhenius rate parameters from the MPE data for minimum retinal radius.
Ω (HSP) is the Arrhenius integral for HSP stimulation.

Damage occurs when Ω(dmg)>1, and HSP production occurs when Ω(HSP)>1. Accordingly, the desired treatment result is for Ω(dmg)<1 and Ω(HSP)>1.

As Table 2 shows, only the canonical SDM treatment accomplishes this.

Following such treatment with a high-density/low-intensity subthreshold diode micropulse laser there must be treatment verification and monitoring. Responses to the treatment described herein should be detectable by retinal function testing pre-therapeutically. Such tests may include pattern electroretinography (PERG), microperimetry, and threshold micro-visual acuity testing, which are all existing technologies. Such post-treatment, pre-therapeutic retinal function testing allows for conformation of treatment administration and effect. It also allows one to prospectively follow patients to determine the need for retreatment, indicated by worsening results of retinal function testing. By combining retinal function testing with true-subthreshold treatment allows for a treatment modality able to demonstrate a desired immediate treatment effect absent detectable retinal damage. The retinal function testing also allows for the prevention of disease progression by detecting early on a need for re-treatment prophylactically.

Current retinal treatment measures are anatomic, meaning that they are "late"-term indicators—abnormal only in advanced and end-stage diseases. Using retinal function indicators that may improve in apparently normal eyes prior to the development of anatomic changes can help document treatment benefits in the absence of anatomic derangement. The retinal function testing can be used to signal the need for re-treatment prior to the development of anatomic disease. The ability to prevent clinical/anatomic disease, vision loss, and the need for more intensive and expensive treatments can be rationally minimized.

Figure 3:
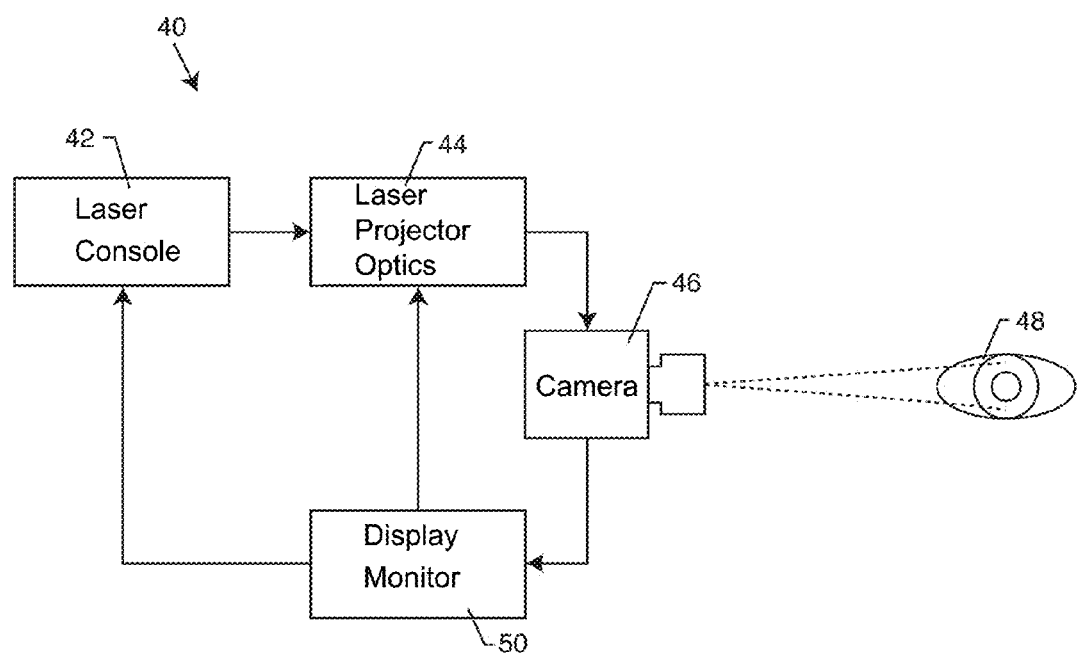
FIG. 3 is a diagrammatic view illustrating a system used for treating a retinal disease or disorder in accordance with the present invention.

With reference now to FIG. 3, a schematic diagram is shown of a system for realizing the process of the present invention. The system, generally referred to by the reference number 40, includes a laser console 42, such as for example the 810 nm near infrared micropulsed diode laser in the preferred embodiment. The laser generates a laser light beam which is passed through an optical lens or mask, or a plurality of optical lenses and/or masks 44 as needed. The laser projector optics 44 pass the shaped light beam to a coaxial wide-field non-contact digital optical viewing system/camera 46 for projecting the laser beam light onto the eye 48 of the patient. It will be understood that the box labeled 46 can represent both the laser beam projector as well as a viewing system/camera, which might in reality comprise two different components in use. The viewing system/camera 46 provides feedback to a display monitor 50, which may also include the necessary computerized hardware, data input and controls, etc. for manipulating the laser 42, the optics 44, and/or the projection/viewing components 46.

Figure 4:
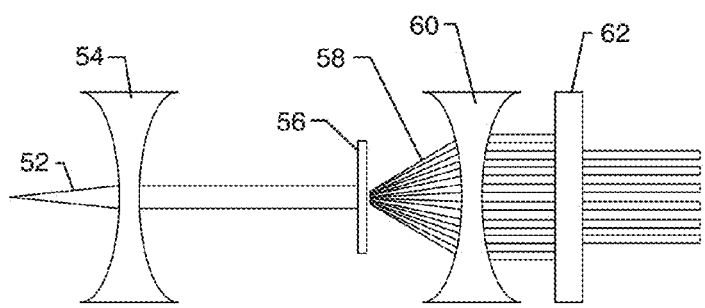
FIG. 4 is a diagrammatic view of an exemplary optical lens or mask used to generate a geometric pattern, in accordance with the present invention.

With reference now to FIG. 4, in one embodiment, the laser light beam 52 is passed through a collimator lens 54 and then through a mask 56. In a particularly preferred embodiment, the mask 56 comprises a diffraction grating. The mask/diffraction grating 56 produces a geometric object, or more typically a geometric pattern of simultaneously produced multiple laser spots or other geometric objects. This is represented by the multiple laser light beams labeled with reference number 58. Alternatively, the multiple laser spots may be generated by a plurality of fiber optic wires. Either method of generating laser spots allows for the creation of a very large number of laser spots simultaneously over a very wide treatment field, such as consisting of the entire retina. In fact, a very high number of laser spots, perhaps numbering in the hundreds even thousands or more could cover the entire ocular fundus and entire retina, including the macula and fovea, retinal blood vessels and optic nerve. The intent of the process in the present invention is to better ensure complete and total coverage and treatment, sparing none of the retina by the laser so as to improve vision.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements. The laser light passing through the mask 56 diffracts, producing a periodic pattern a distance away from the mask 56, shown by the laser beams labeled 58 in FIG. 4. The single laser beam 52 has thus been formed into hundreds or even thousands of individual laser beams 58 so as to create the desired pattern of spots or other geometric objects. These laser beams 58 may be passed through additional lenses, collimators, etc. 60 and 62 in order to convey the laser beams and form the desired pattern on the patient's retina. Such additional lenses, collimators, etc. 60 and 62 can further transform and redirect the laser beams 58 as needed.

Arbitrary patterns can be constructed by controlling the shape, spacing and pattern of the optical mask 56. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Typically, the system of the present invention incorporates a guidance system to ensure complete and total retinal treatment with retinal photostimulation. As the treatment method of the present invention is harmless, the entire retina, including the fovea and even optical nerve, can be treated. Moreover, protection against accidental visual loss by accidental patient movement is not a concern. Instead, patient movement would mainly affect the guidance in tracking of the application of the laser light to ensure adequate coverage. Fixation/tracking/registration systems consisting of a fixation target, tracking mechanism, and linked to system operation are common in many ophthalmic diagnostic systems and can be incorporated into the present invention.

Figure 5:
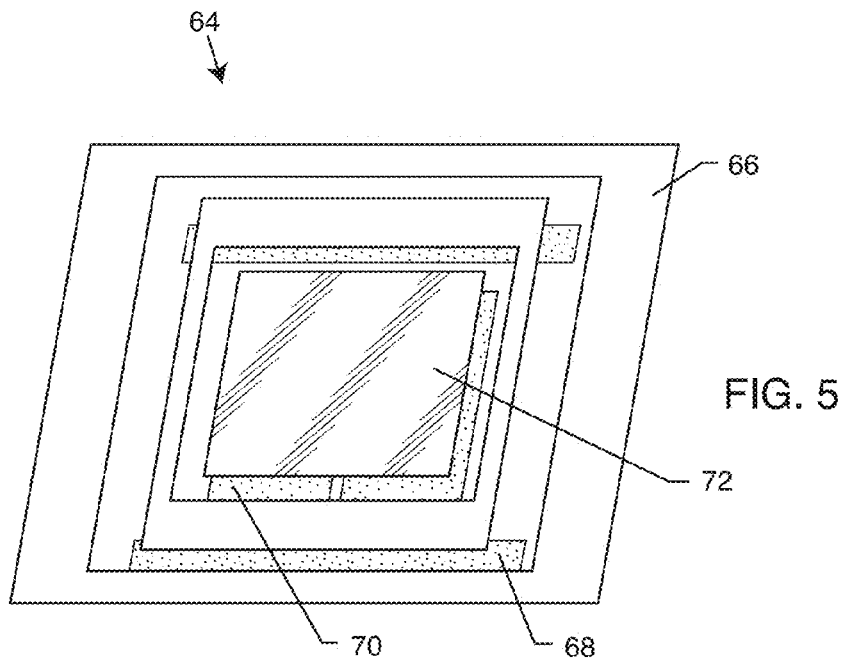
FIG. 5 is a top plan view of an optical scanning mechanism, used in accordance with the present invention.
Figure 6:
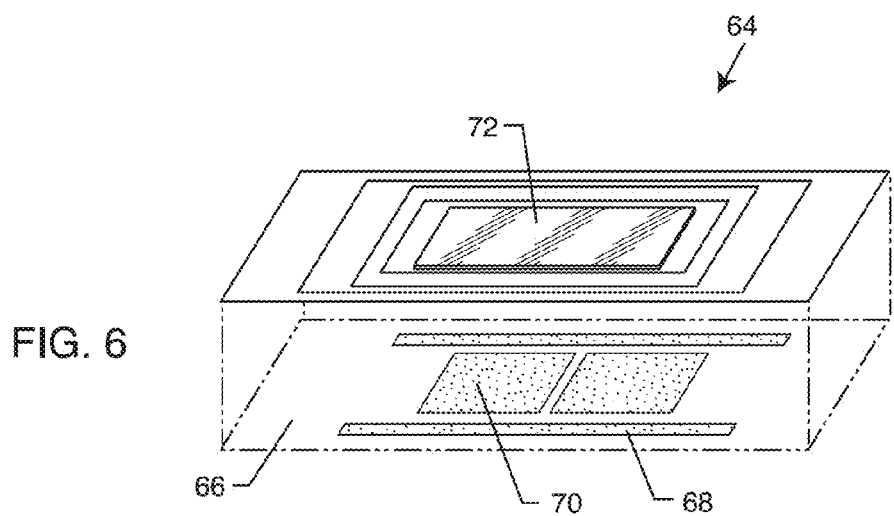
FIG. 6 is a partially exploded view of the optical scanning mechanism of FIG. 5, illustrating the various component parts thereof.

With reference now to FIGS. 5 and 6, in a particularly preferred embodiment, the geometric pattern of simultaneous laser spots is sequentially offset so as to achieve confluent and complete treatment of the retinal surface. Although a segment of the retina can be treated in accordance with the present invention, more ideally the entire retina will be treated with one treatment. This is done in a time-saving manner by placing hundreds to thousands of spots over the entire ocular fundus at once. This pattern of simultaneous spots is scanned, shifted, or redirected as an entire array sequentially, so as to cover the entire retina.

This can be done in a controlled manner using an optical scanning mechanism 64 such as that illustrated in FIGS. 5 and 6. FIGS. 5 and 6 illustrate an optical scanning mechanism 64 in the form of a MEMS mirror, having a base 66 with electronically actuated controllers 68 and 70 which serve to tilt and pan the mirror 72 as electricity is applied and removed thereto. Applying electricity to the controller 68 and 70 causes the mirror 72 to move, and thus the simultaneous pattern of laser spots or other geometric objects reflected thereon to move accordingly on the retina of the patient. This can be done, for example, in an automated fashion using electronic software program to adjust the optical scanning mechanism 64 until complete coverage of the retina, or at least the portion of the retina desired to be treated, is exposed to the phototherapy. The optical scanning mechanism may also be a small beam diameter scanning galvo mirror system, or similar system, such as that distributed by Thorlabs. Such a system is capable of scanning the lasers in the desired offsetting pattern.

As discussed above, it is conventional thinking that tissue damage and lesions must be created in order to have a therapeutic effect. However, the inventors have found that this simply is not the case. In the absence of laser-induced retinal damage, there is no loss of functional retinal tissue and no inflammatory response to treatment. Adverse treatment effects are thus completely eliminated and functional retina tissue is preserved rather than sacrificed. This may yield superior visual acuity results compared to conventional photocoagulation treatment.

Although the inventive system and method has application with many different kinds of tissues, the inventors have particularly studied its applicability in the treatment of retinal tissues and surrounding tissues. Age-related macular degeneration (NAMD) and related disease states are particularly problematic conditions encountered by ophthalmologists. Pharmacologic inhibitors of vascular endothelial growth factor (VEGF)—anti-VEGF medications—have become the mainstay of treatment for choroidal neovascularization that complicates NAMD. Such treatment is currently the most effective intervention to reduce macular exudation, arrest CNVM growth, and most importantly, reduce the risk of visual loss. Thus, ineffectiveness of anti-VEGF medication presents a serious and sight-threatening problem for which there are currently no comparably effective alternatives.

Current intravitreal anti-VEGF medications employ pharmacologic (large) doses of medication designed to temporarily remove, by binding, VEGF from the vitreous cavity, retina and submacular space. The main source of VEGF in the retina is the retinal pigment epithelium (RPE). The causes of local regulatory dysfunction and over-production of VEGF by the RPE in NAMD are complex and not fully understood. VEGF production is linked to the expression of many other factors, the absolute levels and balance of which may be altered with great clinical effect in various disease states, and in response to various treatments, including drugs and conventional retinal laser treatment.

Anti-VEGF injections, typically administered on a near-monthly basis for years, tend to lose effectiveness with repeated use. Use of higher dosages may improve effectiveness in some cases. The gradual loss of drug effect that may, at times, respond to increased drug dosing is termed drug "tolerance". Drug tolerance is generally a permanent condition. This is distinguished from tachyphylaxis, in which the loss of drug response tends to develop almost immediately, is not dose-dependent, and may also resolve after a period of non-treatment. Thus, tolerance appears to best describe the typical loss of response to anti-VEGF treatment of NAMD; and the development of proliferative disease in some eyes despite long-term pharmacologic therapy for diabetic macular edema (DME). In some cases, patients who become unresponsive (tolerant) to one anti-VEGF drug will respond to a different anti-VEGF drug. However, some of these patients eventually become tolerant and unresponsive to all available anti-VEGF medications. Verteporfin photodynamic therapy has been reported to be beneficial as "rescue therapy" in such cases. But, at this point in time, loss of anti-VEGF monotherapy effectiveness generally bodes ill for the visual prognosis.

SDM treatment was first described in 2005. By definition, SDM does not cause tissue damage and has no known adverse treatment effect. SDM has been reported to be an effective treatment in a number of retinal disorders, including DME, proliferative diabetic retinopathy (PDR), macular edema due to branch retinal vein occlusion (BRVO), and central serous chorioretinopathy (CSR). The safety of SDM is such that it may be used transfoveally in eyes with 20/20 visual acuity to reduce the risk of visual loss due to early fovea-involving DME. It has been suggested that SDM works by targeting, preserving, and normalizing—moving toward normal—function of the RPE. Tolerance to anti-VEGF medication appears to develop via drug-induced disturbance of RPE auto-regulation resulting in altered cytokine expression. By defining "normal" in this setting as the state of the RPE initially responsive to drug therapy, it is believed that SDM might reverse drug tolerance by restoring drug sensitivity in eyes with NAMD no longer responsive to anti-VEGF therapy.

Figure 7:
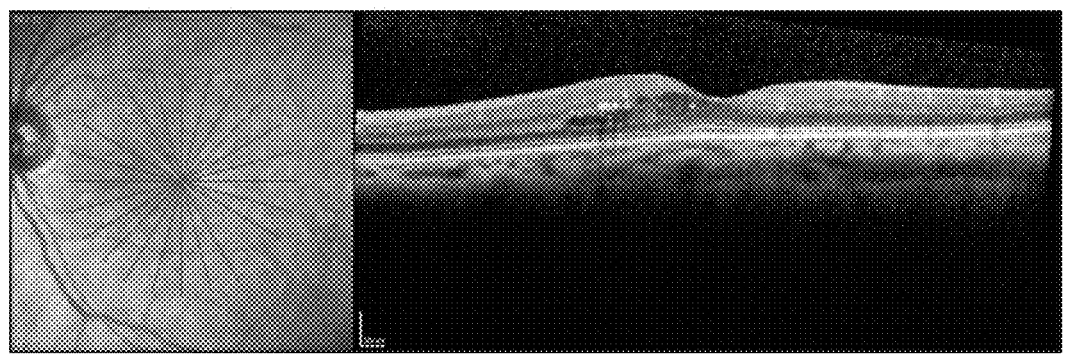
FIG. 7 is an illustration of a cross-sectional view of a diseased human retina before treatment with the present invention.
Figure 8:
FIG. 8 is a cross-sectional view similar to FIG. 7, illustrating the portion of the retina after treatment using the present invention.

With reference now to FIGS. 7 and 8, spectral-domain OCT imaging is shown in FIG. 7 of the macular and foveal area of the retina before treatment with the present invention. FIG. 8 is of the optical coherence tomography (OCT) image of the same macula and fovea after treatment using the present invention, using a 131 micrometer retinal spot, 5% duty cycle, 0.3 second pulse duration, 0.9 watt peak power placed throughout the area of macular thickening, including the fovea. It will be noted that the enlarged dark area to the left of the fovea depression (representing the pathologic retinal thickening of diabetic macular edema) is absent, as well as the fact that there is an absence of any laser-induced retinal damage. Such treatment simply would not be attainable with conventional techniques.

SDM Trial Study #1

In a particular study of SDM treatment of drug tolerant NAMD, the inventors selected patients according to certain select criteria. A candidate for SDM treatment must have been diagnosed with NAMD requiring intravitreal injections of anti-VEGF medication with initial medication effectiveness and subsequent development of drug non-responsiveness. The diagnosis must have been defined by persistence or worsening of subretinal fluid (SRF) and/or cystoid macular edema (CME) by spectral-domain optical coherence tomography (OCT) despite at least four consecutive anti-VEGF injections, including at least three consecutive injections of Aflibercept given weeks apart. The patient then received SDM treatment after diagnosis of the drug tolerance with resumption of Aflibercept one month after a single treatment session of SDM and at least two months follow-up after the SDM treatment.

One month after the final clinically ineffective Aflibercept injection, SDM was performed. At the time of treatment, the patient's pupils were dilated and topical proparacaine was applied to the cornea. A Mainster macular contact lens (magnification factor 1.05×, Ocular Instruments, Bellevue, Wash.) was placed on the cornea with viscoelastic solution. Confluent application of contiguous SDM laser spots were then placed over the entire area of the CNVM and subretinal fluid as indicated by pre-treatment intravenous fundus fluorescein angiography, OCT, and contact lens examination. Treatment was performed transfoveally and extended slightly (~500 µm) past the margins of the lesion and exudation into "dry" macula circumferentially to ensure complete treatment coverage. Effort was made to focus the laser on the RPE beneath the SRF and/or CME, including any underlying retinal pigment epithelial detachment (PED), if present. Laser parameters included use of an 810 nm micropulsed diode laser (Oculight SLx, Iridex Corp., Mountain View, Calif.) with a 300 µm aerial spot; 2.0 Watt power, 5% micropulse duty cycle, and 0.20 second exposure duration. Treatment generally employed application of at least 400-1200 spots or more (~200-300 spots per disc diameter), depending on the area to be covered.

In a prior study of SDM for DME, the effects of treatment developed gradually, usually beginning to be notable by OCT at one month postoperatively and continuing to improve thereafter. Based on this observation, retreatment with Aflibercept was delayed until one month after SDM treatment to ensure adequate time was allowed for the effects the SDM treatment would elicit to become manifest prior to re-exposure to Aflibercept. All patients continued to be followed monthly and treated as necessary with Aflibercept thereafter.

A total of 13 eyes of 12 patients were included for study. Subjects averaged 84 years old at the time of SDM treatment (range 73-97 years). The average follow-up post-SDM was 5 months (range 3-7 months). Prior to SDM treatment the eyes received 16-67 intravitreal anti-VEGF injections (average 34) for neovascular AMD. Exudation unresponsive to drug treatment prior to SDM included SRF alone in 9 eyes (69%), CME and SRF in 2 eyes (15%), and CME alone in 2 eyes (15%). Prior to SDM, 6 eyes (46%) had concurrent PED. The average pre-SDM CFT was 349 µm (SD=102 µm), average pre-SDM MMT was 435 µm (SD=111 um), and average Log MAR VA was 0.33 (SD=0.11).

Comparisons between pre-SDM and post-SDM measures of CFT, MMT, and log MAR VA showed improvement. CFT showed significant reductions at 3, 4, and 5 months post-SDM compared to pre-SDM (decreases of 67, 93, and 103 µm respectively; all p≤0.0605). In addition, CFT measured at 2-5 month post-SDM, after re-injection of Aflibercept, was significantly improved compared to CFT 1 month post-SDM and prior to re-injection (decreased between 61 and 95 µm; all p≤0.0391). MMT showed similar improvement from pre-SDM and 1 month post-SDM measures. Specifically, MMT showed a marginally significant improvement of 41 µm at 2 months post-SDM (p=0.0640), and significant improvements of 65, 103, and 105 µm at 3, 4, and 5 months post-SDM, respectively, compared to pre-SDM (all p≤0.0327). In addition, MMT showed significant reductions post-SDM and after re-injection of Aflibercept compared to 1 month post-SDM which was prior to re-injection (all p≤0.0547). VA showed no significant pre- to post-SDM differences or differences between 1 month post-SDM and subsequent follow-up visits.

Overall, 12/13 eyes (92%) improved, with complete resolution of macular exudation achieved in 9/13 eyes (69%). PED improved or resolved in 3/6 eyes (50%). One eye did not respond to SDM treatment. This eye had the most confluent and complete submacular pigment atrophy by fundus autofluorescence photography. All eyes that improved following SDM treatment continued to be responsive to Aflibercept throughout the course of follow-up. There were no adverse treatment effects due to SDM.

SDM Trial Study #2

In another study SDM was performed in consecutive eyes that were unresponsive to all anti-VEGF medications. Loss of drug response, or tolerance to the drugs, was defines as at least four consecutive monthly drug injections without improvement according to OCT, including at least two consecutive final monthly injections of aflibercept. One month after the last ineffective aflibercept injection, SDM treatment was performed. No anti-VEGF drugs were injected at the time of SDM treatment so as not to interfere with the development of the effects of SDM on the RPE. One month after SDM treatment, each eye was reevaluated by OCT and monthly aflibercept therapy resumed.

This study involved ten eyes of nine different patients, aged 74-97 years that had a tolerance for anti-VEGF drugs. The number of pre-SDM drug injections, including bevacizumab, ranibizumab, and aflibercept, ranged from 4-67 per eye with an average of 29. Nine eyes were tolerant to all listed drugs. One eye was not treated with ranibizumab before SDM treatment, but was unresponsive to bevacizumab and aflibercept. A single SDM treatment was performed in each eye after confirmation of drug tolerance. At the time of SDM treatment, five eyes had serious pigment epithelial detachment and visual acuities ranged from 20/30 to 20/60.

One month after SDM treatment, two eyes were insignificantly improved with a slight reduction of sub-retinal fluid and four eyes were significantly worsened per OCT. Aflibercept therapy was resumed one month post-SDM treatment. Two months post-SDM treatment and one month after resumed aflibercept treatment, eight of the ten eyes were improved with complete resolution of exudation in two eyes. Three months after SDM treatment with a second post-SDM injection of aflibercept in the second month, all ten eyes were improved with complete resolution of exudation in six eyes. Central foveal thickness and maximum macular thickness were both significantly improved. Overall visual acuity was unchanged. No eyes showed evidence of adverse treatment effect or laser-induced retinal damage.

Tolerance, or acquired loss of drug response, is a common condition that can develop to different drugs, in different cell types, in different ways. When tolerance develops to one drug, cross-tolerance to drugs of the same family is often also observed. Tolerance may be partial, or complete. Innate drug insensitivity, which may be genetically determined, is distinguished from tolerance by a poor initial drug response as well. Depending upon the clinical setting, the development of drug tolerance can have grave prognostic implications. While drug tolerance is generally permanent, pharmacologic reversal of drug tolerance has been reported in the laboratory. To our knowledge, this is the first report of clinically effective reversal of drug tolerance in humans.

Normal physiologic homeostasis and disease response are mediated by trophic factors produced by immune, hematopoietic and neural cells. These include cytokines; small proteins manifold in type and effects, and powerful locally in very small amounts. Production of any one cytokine is generally linked to others by complex autoregulatory mechanisms. The clinical effects of these factors, such as VEGF, are complex and variable, reflecting both their absolute levels, as well as levels relative to other factors. In the retina, the most important cytokine source is the RPE. SDM selectively targets the RPE.

While there are many RPE mediated factors—both known and unknown—working in innumerable combinations to produce diverse effects, the potentialities of the RPE are finite. Thus, RPE-sourced cytokines play important roles in most, if not all, retinal disorders. To the extent that RPE cytokine expression is alike, such as DME and BRVO, treatments targeting common factors tend to be effective for both disorders. Retinal disorders that are more different, such as DME and CSR, tend to exhibit different cytokine associations, and thus different responses to targeted drug therapy, such as anti-VEGF medication. Despite such differences, SDM has been found to be of benefit in retinal disorders as disparate as metabolic and occlusive retinal vascular disease, CSR, and now drug tolerant NAMD. SDM does this without inducing any morphologic change in the retina or RPE, or causing even transient break down in the blood-retinal barrier. Thus, SDM causes no inflammation or loss of visual function. Because SDM is salutary in unrelated retinal disorders, SDM appears to exert its influence prior to retinal cytokine expression. Thus, SDM appears to normalize the behavior, and consequent cytokine production, of RPE cells affected but unharmed by SDM exposure.

Despite a near infinite variety of possible cellular abnormalities, cells of all types share a common and highly conserved mechanism of repair: heat shock proteins (HSPs). HSPs are elicited almost immediately, in seconds to minutes, by almost any type of cell stress or injury. In the absence of lethal cell injury, HSPs are extremely effective at repairing and returning the viable cell toward a more normal functional state. Although HSPs are transient, generally peaking in hours and persisting for a few days, their effects may be long lasting. HSPs reduce inflammation, a common factor in many retinal disorders, including diabetic retinopathy (DR) and AMD.

Laser treatment induces HSP production and, in the case of retinal treatment, alters retinal cytokine expression. The more sudden and severe the non-lethal cellular stress (such as laser irradiation), the more rapid and robust HSP production. Thus, a burst of repetitive low temperature thermal spikes at a very steep rate of change (~70° C. elevation with each 100 μs micropulse, or 70,000° C./sec) produced by each SDM exposure is especially effective in stimulating production of HSPs, particularly compared to non-lethal exposure to subthreshold treatment with continuous wave lasers, which can duplicate only the low average tissue temperature rise.

Laser wavelengths below 550 nm produce increasingly cytotoxic photochemical effects. At 810 nm, SDM produces photothermal, rather than photochemical, cellular stress. Thus, SDM is able to affect the tissue, including RPE, without damaging it. Consistent with HSP activation, SDM produces prompt clinical effects, such as rapid subjective visual improvement and improved macular sensitivity measured by microperimetry, as well as long-term effects, such as reduction of DME and involution of retinal neovascularization.

In the retina, the clinical benefits of SDM are thus produced by sub-morbid photothermal RPE HSP activation. In dysfunctional RPE cells, HSP stimulation by SDM results in normalized cytokine expression, and consequently improved retinal structure and function. The therapeutic effects of this "low-intensity" laser/tissue interaction are then amplified by "high-density" laser application, recruiting all the dysfunctional RPE in the targeted area, thereby maximizing the treatment effect. These principles define the treatment strategy of SDM described herein. The ability of SDM to produce therapeutic effects similar to both drugs and photocoagulation indicates that laser-induced retinal damage (for effects other than cautery) is unnecessary and non-therapeutic; and, in fact, detrimental because of the loss of retinal function and incitement of inflammation.

Because normally functioning cells are not in need of repair, HSP stimulation in normal cells would tend to have no notable clinical effect. The "patho-selectivity" of near infrared laser effects, such as SDM, on various cell types is consistent with clinical observations of SDM. This facility is key to the suitability of SDM for early and preventative treatment of eyes with chronic progressive disease and eyes with minimal retinal abnormality and minimal dysfunction. Finally, SDM has been reported to have a clinically broad therapeutic range, consistent with American National Standards Institute "Maximum Permissible Exposure" predictions. While SDM may cause direct photothermal effects such as entropic protein unfolding and disaggregation, SDM appears optimized for clinically safe and effective stimulation of HSP-mediated retinal repair.

As noted above, while SDM stimulation of RPE HSPs is non-specific with regard to the disease process, the result of HSP mediated repair is by its nature specific to the state of the dysfunction. HSPs tend to fix what is wrong, whatever that might be. Thus, the observed effectiveness of SDM in retinal conditions as widely disparate as BRVO, DME, PDR, CSR, and drug-tolerant NAMD. Conceptually, this facility can be considered a sort of "Reset to Default" mode of SDM action. For the wide range of retinal disorders in which RPE function is critical, SDM normalizes RPE function by triggering a "reset" (to the "factory default settings") via HSP-mediated cellular repair. Certainly, SDM has limitations. For instance, clinical experience with this theory suggests that SDM is less effective once RPE mediated disease-related anatomic derangement, such as in chronic cystoid macular edema, or the pathologic environment, is so severe and/or degenerative that the retina can no longer respond to RPE autoregulatory influences. That absence of sufficient viable target RPE due to severe pigmentary atrophy may preclude a treatment response. In addition, cells already committed to apoptosis or necrosis may be unable to respond to laser-stimulated HSP mediated repair. Indeed, these may account in part for the reduced effectiveness of all therapeutic modalities in advanced disease, again underscoring the importance of early and preventive treatment.

The severity of disease in advanced NAMD suggested that SDM would not likely be an effective monotherapy in such drug-tolerant eyes. However, the reset theory also suggested that SDM might reverse anti-VEGF drug tolerance. In the case of drug tolerance, the "default" or "normal" state of the RPE was defined as that initially responsive to anti-VEGF medications. The "abnormal" state was defined as the condition of drug tolerance, representing RPE dysfunction developing in response to chronic and repeated pharmacologic drug exposures. In the above described study, the laser-induced re-sensitization of the RPE did indeed occur pursuant to the reset theory, reversing drug tolerance and allowing resumption of clinically effective anti-VEGF therapy. The absence of known SDM adverse treatment affects allows for consideration of early and preventive treatment, liberal application and re-treatment as necessary. The reset theory also suggests that SDM may have application to many different types of RPE-mediated retinal disorders beyond those thus far reported. In the above study, no eyes treated with SDM for DME presenting with good visual acuity required anti-VEGF injections post-treatment. In another study of SDM, fewer than 10% of eyes treated for DME presenting with a visual acuity of greater than 20/40 required use of intravitreal anti-VEGF medication over a median twelve months follow up. In another study, panretinal SDM was noted to reduce the rate of progression of severe non-proliferative and proliferative diabetic retinopathy. On the other hand, while most SDM effects appear to be long-lasting if not permanent, the reset theory and clinical observations suggest that SDM can appear to "wear off" on occasion, such as in some cases of DME.

Based upon the above information and studies, SDM treatment may directly affect cytokine expression and heat shock protein (HSP) activation in the targeted tissue, particularly retinal pigmented epithelium (RPE) layer.

Figure 9:
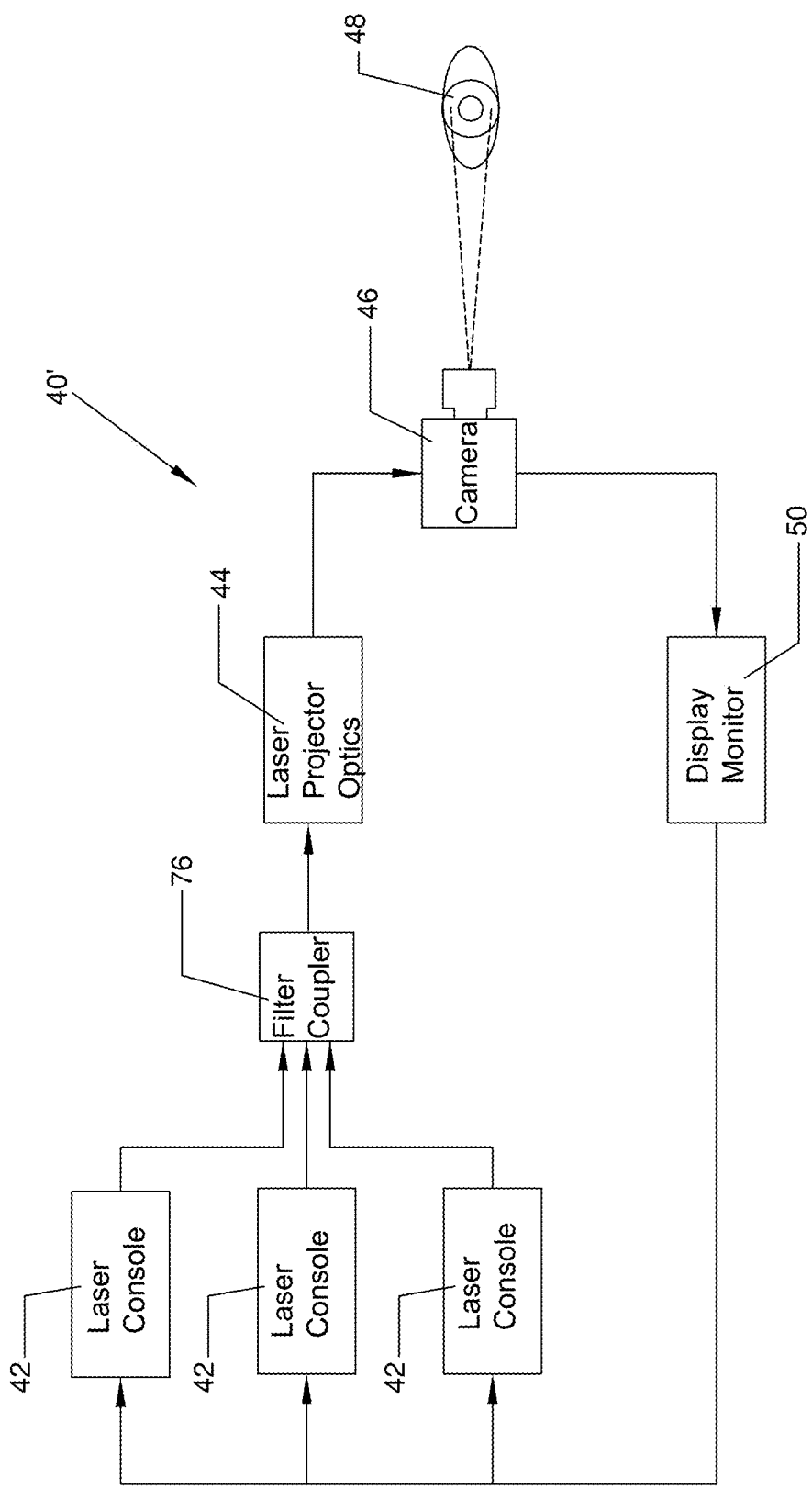
FIG. 9 is a diagrammatic view illustrating an alternate embodiment of a system used for treating a retinal disease or disorder in accordance with the present invention.

FIG. 9 illustrates diagrammatically a system which couples multiple light sources into the pattern-generating optical subassembly described above. Specifically, this system 40' is similar to the system 40 described in FIG. 3 above. The primary differences between the alternate system 40' and the earlier described system 40 is the inclusion of a plurality of laser consoles 42, the outputs of which are each fed into a fiber coupler 76. The fiber coupler produces a single output that is passed into the laser projector optics 44 as described in the earlier system. The coupling of the plurality of laser consoles 42 into a single optical fiber is achieved with a fiber coupler 76 as is known in the art. Other known mechanisms for combining multiple light sources are available and may be used to replace the fiber coupler described herein.

In this system 40' the multiple light sources 42 follow a similar path as described in the earlier system 40, i.e., collimated, diffracted, recollimated, and directed into the retina with a steering mechanism. In this alternate system 40' the diffractive element must function differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the steering mechanism 46 to the retina 48 for treatment. The slight difference in the diffraction angles will affect how the steering pattern achieves coverage of the retina.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the retina, the application of the other wavelengths achieves either incomplete or overlapping coverage of the retina. The second mode sequentially applies each light source of a varying wavelength with the proper steering pattern to achieve complete coverage of the retina for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 10:
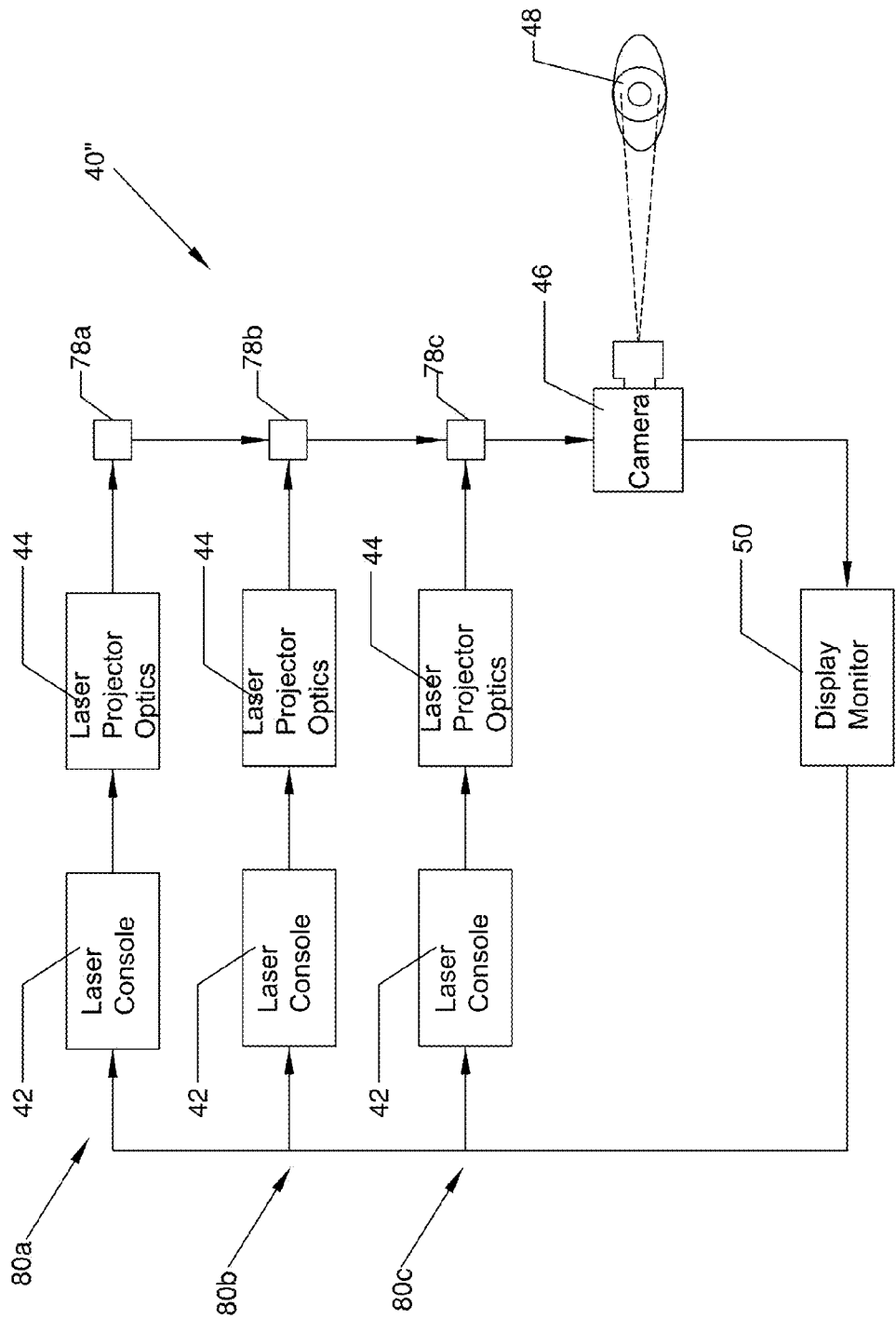
FIG. 10 is a diagrammatic view illustrating yet another alternate embodiment of a system used for treating a retinal disease or disorder in accordance with the present invention.

FIG. 10 illustrates diagrammatically yet another alternate embodiment of the inventive system 40". This system 40" is configured generally the same as the system 40 depicted in FIG. 3. The main difference resides in the inclusion of multiple pattern-generating subassembly channels tuned to a specific wavelength of the light source. Multiple laser consoles 42 are arranged in parallel with each one leading directly into its own laser projector optics 44. The laser projector optics of each channel 80a, 80b, 80c comprise a collimator 54, mask or diffraction grating 56 and recollimators 60, 62 as described in connection with FIG. 4 above—the entire set of optics tuned for the specific wavelength generated by the corresponding laser console 42. The output from each set of optics 44 is then directed to a beam splitter 78 for combination with the other wavelengths. It is known by those skilled in the art that a beam splitter used in reverse can be used to combine multiple beams of light into a single output.

The combined channel output from the final beam splitter 78c is then directed through the camera 46 which applies a steering mechanism to allow for complete coverage of the retina 48.

In this system 40" the optical elements for each channel are tuned to produce the exact specified pattern for that channel's wavelength. Consequently, when all channels are combined and properly aligned a single steering pattern may be used to achieve complete coverage of the retina for all wavelengths.

The system 40" may use as many channels 80a, 80b, 80c, etc. and beam splitters 78a, 78b, 78c, etc. as there are wavelengths of light being used in the treatment.

Implementation of the system 40" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 40", each channel begins with a light source 42, which could be from an optical fiber as in other embodiments of the pattern-generating subassembly. This light source 42 is directed to the optical assembly 44 for collimation, diffraction, recollimation and directed into the beam splitter which combines the channel with the main output.

The invention described herein is generally safe for pan-retinal and/or trans-foveal treatment. However, it is possible that a user, i.e., surgeon, preparing to limit treatment to a particular area of the retina where disease markers are located or to prevent treatment in a particular area with darker pigmentation, such as from scar tissue.

Although the present invention is particularly suited for treatment of vascular retinal diseases, such as diabetic retinopathy and macular edema, it is contemplated that it could be used for other diseases as well. The system and process of the present invention could target the trabecular mesh work as treatment for glaucoma, accomplished by another customized treatment field template. It is contemplated by the present invention that the system and concepts of the present invention be applied to phototherapy treatment of other tissues, such as, but not limited to, the gastrointestinal or respiratory mucosa, delivered endoscopically, for other purposes.

Although several embodiments have been described in detail for purposes of illustration, various modifications may be made without departing from the scope and spirit of the invention. Accordingly, the invention is not to be limited, except as by the appended claims.

What is claimed is:

1. A process for restoring responsiveness to medication in retinal tissue comprising the steps of: generating a confluent, contiguous laser light beam from a laser source; optically shaping the laser light beam through an optical lens or mask; exposing the retinal tissue to the laser light beam; and allowing the retinal tissue to recover for a predetermined period of time and then administering medication to which the retinal tissue was unresponsive.

2. The process of claim 1, including the step of dilating a pupil of an eye containing the retinal tissue.

3. The process of claim 1, further comprising the step of applying topical proparacaine to a cornea of the eye.

4. The process of claim 1, further comprising the step of applying a macular contact lens with viscoelastic fluid.

5. The process of claim 4, wherein the macular contact lens has a magnification factor of 1.05×.

6. The process of claim 1, wherein the exposing step includes exposing the laser light beam to the entire retina.

7. The process of any of claims 1 and 2-6, wherein the confluent, contiguous laser light beam comprises a subthreshold diode micropulse laser beam.

8. The process of claim 7, wherein the subthreshold diode micropulse laser beam has a high-density comprising between 400 and 1200 spots in a 300 micron treatment area.

9. The process of claim 7, wherein the subthreshold diode micropulse laser beam has a wavelength between 750 nm-1300 nm at 2.0 Watts.

10. The process of claim 9, wherein the wavelength is approximately 810 nm.

11. The process of claim 7, wherein the subthreshold diode micropulse laser beam has a duty cycle of less than 10% and a 0.02 second exposure duration.

12. The process of claim 11, wherein the duty cycle is approximately 5%.

13. The process of claim 7, wherein the subthreshold diode micropulse laser beam has a pulse length of 500 milliseconds or less.

14. The process of claim 13, wherein the pulse length is 20 milliseconds.

15. The process of claim 1, wherein the predetermined period of time is one month.

16. The process of claim 1, wherein the optically shaping step includes diffracting the laser light beam so as to produce a periodic pattern.

17. The process of claim 16, wherein the periodic pattern comprises a multitude of individual spots.

18. The process of claim 17, wherein the optically shaping step includes sequentially offsetting the multitude of individual spots so as to completely cover the retinal tissue.

\* \* \* \* \*